United States Patent [19]

Latour, Jr. et al.

[11] Patent Number: 4,858,473

[45] Date of Patent: Aug. 22, 1989

[54] MINIATURE CLOSED-LOOP DYNAMIC UNIVERSAL MECHANICAL TESTING MACHINE

[75] Inventors: Robert A. Latour, Jr., Narberth; Jonathan Black, King of Prussia, both of Pa.

[73] Assignee: Trustees of the University of Pennsylvania, Philadelphia, Pa.

[21] Appl. No.: 208,747

[22] Filed: Jun. 17, 1988

[51] Int. Cl.[4] .............................................. G01N 3/00
[52] U.S. Cl. .................................................... 73/805
[58] Field of Search ...................... 73/805, 862.65, 826

[56] References Cited

U.S. PATENT DOCUMENTS 3,359,789  12/1967  Forse .......................... 73/862.65 X

FOREIGN PATENT DOCUMENTS 61946  5/1955  France .............................. 73/862.65

OTHER PUBLICATIONS

Busnell, A. R. et al., An Apparatus for Fatigue-Testing of Fibres, J. Phys. E, vol. 4, No. 11, Nov. 1971, Gt. Britain, pp. 868-872.

Primary Examiner—Jerry W. Myracle
Attorney, Agent, or Firm—Woodcock Washburn Kurtz Mackiewicz & Norris

[57] ABSTRACT

Mechanical testing apparatus and methods are disclosed for providing closed-loop dynamic mechanical testing under small loads. The testing machine includes an electrically-driven actuator and light weight load transducer. The load transducer converts the applied load into a voltage feedback signal, which is then fed into a closed-loop control means for regulating the applied load in response, in part, to the voltage feedback signal. The testing machine is extremely sensitive and is capable of testing samples with an applied load force of less than about 20 grams.

23 Claims, 2 Drawing Sheets

U.S. Patent   Aug. 22, 1989   Sheet 1 of 2   4,858,473
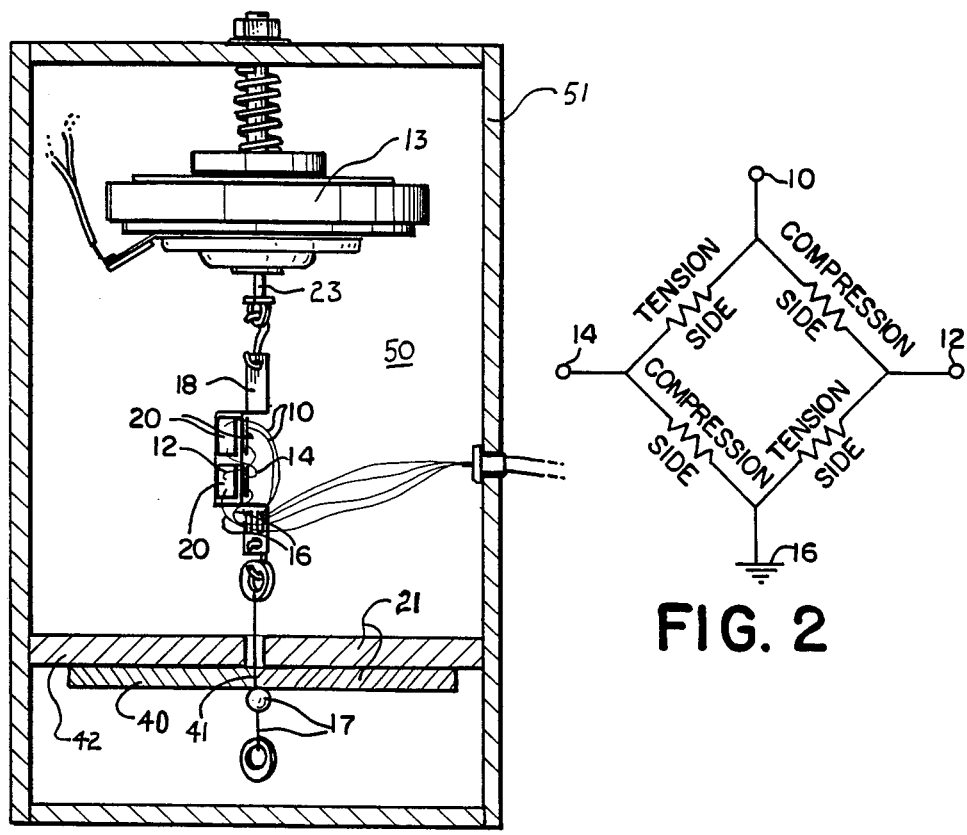
FIG. 1
FIG. 2
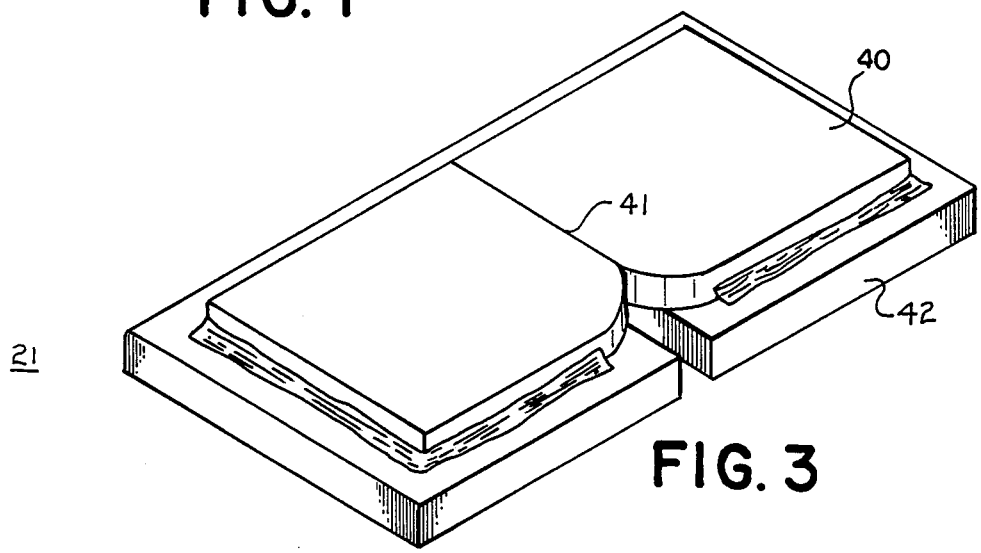
FIG. 3

MINIATURE CLOSED-LOOP DYNAMIC UNIVERSAL MECHANICAL TESTING MACHINE

FIELD OF THE INVENTION

This invention relates to lightweight testing machines and more particularly, to closed-loop load control mechanical testing machines which can be used for controlled load testing at loads below about 200 grams.

BACKGROUND OF THE INVENTION

Present day mechanical testing machines are multi-use machines with load testing capacities from about 10 to over 1,000 pounds. For material testing applications where very small loads are required, for example about 0.5 to 15 grams (0.001–0.03 pounds), the extra expense associated with these larger machines becomes economically prohibitive for many research endeavors. Smaller and less expensive mechanical testing apparatus have been developed, however, these generally do not incorporate closed-loop controls which are necessary for controlled load fatigue testing.

There is a particular need for an inexpensive, and lightweight, mechanical testing apparatus suitable for testing the fiber-matrix interfacial bond in fiber-reinforced plastic materials. Typically, a model consisting of a single fiber imbedded within a small droplet of plastic is employed for testing this bond. The test requires the application of controlled loads in the range of about 0.5 to 15 grams. Of particular interest to those in the field has been the fatigue behavior of the interface of such samples which requires the testing of multiple samples, each of which may take up to a few days to complete. Since large numbers of specimens are needed to characterize fatigue processes, it is thus desirable to have several independently controlled, simultaneously operating mechanical testing machines, each of which is suitable to be used for controlled load testing the loads below about 20 grams. The closed-loop load control mechanical testing machines presently on the market, which can be used for controlled load testing at loads below about 20 grams, are generally large machines which also can be employed for use with loads of as much as 1,000 pounds. These machines have generally been constructed much heavier and much costlier (about $20,000.–$30,000. each) than what is required for miniature load testing. The smaller versions of these machines are usually less expensive (about $10,000). However, it is understood that these do not have the ability to perform closed-loop control testing.

Accordingly, a need exists for a miniature, relatively inexpensive, closed-loop mechanical testing machine for controlled-load testing with very small peak loads.

SUMMARY OF THE INVENTION

A miniature closed-loop dynamic universal mechanical testing machine and method for testing mechanical specimens, under small loads, are provided. The testing machine includes an electrically-driven actuator means for applying a load upon a test sample and a load transducer means for converting the applied load into a voltage feedback signal. The voltage feedback signal is then fed into a closed-loop control means, which is designed to regulate the applied load force in response, in part, to the voltge feedback signal. The sample to be tested can be either attached between the electrically-driven actuator means and the load transducer means or between the load transducer means and a gripping device with the other end of the load transducer means being coupled directly to the actuator means.

Accordingly, a highly-sensitive and relatively inexpensive mechanical testing apparatus is disclosed which permits the testing of samples with an applied peak load force of less than about 200 grams, preferably less than about 20 grams. By using a simple electrically-operated solenoid as the test machine actuator and coupling it with a sensitive feedback transducer means, this invention creates a closed-loop test machine specifically designed for extremely small load and displacement mechanical testing. This machine should be attractive to those in the art seeking to perform mechanical tests on very delicate materials requiring the accurate application of very small loads and displacements.

OBJECTS OF THE INVENTION

It is an object of this invention to provide a relatively inexpensive mechanical testing machine which permits controlled load testing below about 200 grams.

It is another object of the invention to provide a closed-loop mechanical testing machine suitable for dedicated controlled-load testing for testing under very small loads.

It is a further object of this invention to provide a mechanical testing machine and method for testing miniature samples simultaneously without exorbitant equipment costs.

With these objects in view, this invention resides in the novel construction, combination, arrangement of parts and methods substantially as hereinafter described and more particularly defined by the attached claims.

BRIEF DESCRIPTION OF THE DRAWINGS

The accompanying drawings illustrate one embodiment of the invention.

FIG. 1: is a diagrammatic view of a preferred mechanical testing apparatus of this invention;

FIG. 2: is a Wheatstone-bridge arrangement for the preferred apparatus of FIG. 1;

FIG. 3: is a perspective view of a preferred specimen holding device for testing polymer-fiber specimens.

DETAILED DESCRIPTION OF THE INVENTION

Figure 4:
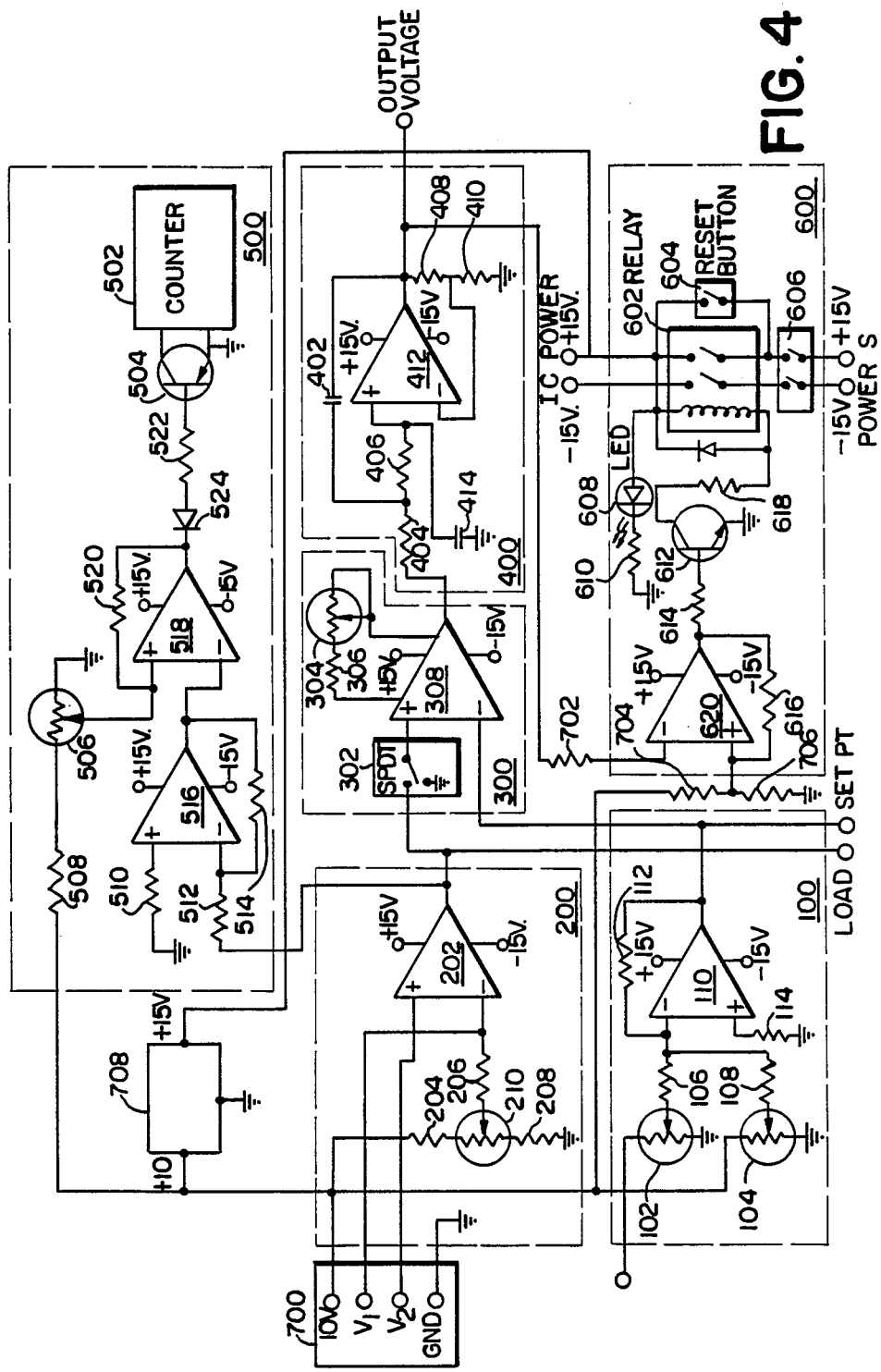
FIG. 4: is a schematic circuit diagram of a preferred closed-loop control means.

The apparatus of this invention provides for the mechanical testing of samples under a relatively light load. The apparatus includes an electrically driven actuator means for exerting an applied load force of not more than about 200 grams, preferably less than about 20 grams, upon a sample. It further includes a load transducer means for converting the applied load force into a voltage feedback signal. The transducer means is attachable to the sample and weighs less than about 10 grams, preferably less than about 1 gram. The apparatus further includes closed-loop control means for at least regulating the applied load force in response, in part, to the voltage feedback signal. The sample, preferably a polymer-fiber composite, can be disposed between the electrically-driven actuator means and the load transducer means, or alternatively, between the load transducer means and a gripping device, such as that represented by FIG. 3.

A more detailed construction for the preferred mechanical testing apparatus 50 of FIG. 1 will now be described. The apparatus 50 preferably includes a miniature load frame 51 driven by a closed-loop electronic control means, more specifically described in FIG. 4. The control means preferably includes an externally connected function generator and power supply. Referring now to FIG. 1, the load frame 51 consists of an electrically driven displacement actuator 13 which is serially coupled to a sensitive, ultra-light load transducer 18. A sample to be tested can be either attached between the actuator 13 and transducer 18 or between the transducer 18 and a grip 21 fixed to the load frame 51 with the other end of the transducer 18 being coupled directly to the actuator 13. The gripping device 21 preferably has a plurality of plates 40 and 42, with a slot 41 for accepting a sample 17 such as a polymeric-fiber sample.

The closed-loop load control involves the generation of an electronic signal to cause the actuator 13 to move upward or downward. This movement, in turn, causes a load to be applied to the sample 17 under the test conditions. The amount of the load applied by the actuator's movement is sensed by the serially coupled load transducer means. The load transducer means sends an electrical signal representative of the applied load, described herein as feedback signal, back to the control means. A feedback signal is then electronically compared to an original set point signal to insure that the desired amount of load has actually been administered to the sample under test. Should the feedback signal begin to drift from the set point signal, the circuitry automatically compensates in manners known to persons of skill in the art to bring the feedback signal back to its proper level. Thus, a closed-loop control is properly maintained by the device and advantageously controls load testing to insure that the desired loads are actually being applied to the test specimen.

The electrically-driven actuator means of FIG. 1 will now be described. The actuator means preferably comprises an electrically driven "push-pull" solenoid, i.e. actuator 13, such as these similar to ones commonly used in audio speakers. The frame of this solenoid is preferably fixed to the load frame 51 while a "push-pull" rod 23 is connected to one end of either the sample 17 or the load transducer 18. In a preferred embodiment, a positive voltage signal applied to the solenoid will cause it to pull upward, and a negative voltage will cause it to push downward.

The load transducer 18 is composed of four high resistance strain gauges 20 bonded to a flexible sheet of material, preferably metallic, and most preferably stainless steel sheet metal of a thickness of about 0.003 inches. The strain gauges 20 are preferably disposed in a Wheatstone-bridge arrangement, per FIG. 2. The sheet metal, or flexible sheet of material, is preferably bent in such a way as to cause a generation of a strain field approximating pure bending along the strain gauge portion of the sheet metal upon the application of an axial tensile force.

As shown in FIGS. 1 and 2, the load transducer 18 has four leads extending from it 10, 12, 14 and 16. Lead 10 is preferably a 10 volt supply voltage from the controller circuitry. Lead 16 preferably connects to ground (zero voltage). Lead 14 and lead 12 are leads whose voltages change as a function of the applied load to the transducer. As the load is applied, voltage in lead 14 will decrease while the voltage in lead 12 will increase. The difference in voltage between lead 14 and lead 12 is what provides the load monitoring feedback signal to the control means. One unique feature of the load transducer 18 is that it is extremely light-weight, i.e., less than about 10 grams, more preferably weighing less than 1 about gram, and even more preferably, less than about 0.2 grams. The light weight construction of the load transducer 18 enables it to be suspended between the actuator 13 and the sample 17 for testing. This is important because the solenoid actuator 13 is limited in the amount of load which it can generate. By minimizing the transducer weight, the amount of load able to be applied to the sample is increased. The low weight of the suspended transducer 18 also improves the frequency response of the test system for dynamic testing, such as that experienced during cyclic loading, i.e. fatigue testing.

Referring to FIG. 4, the preferred closed-loop control means will now be described. The control means can be described as having six principal components: set point adjustment means 100, feedback amplification means 200, comparator means 300, power amplification means 400, load cycle counter means 500 and power trip means 600.

The set point adjustment means 100 requires the input of an external function generator to specify the type of waveform and frequency to be followed if dynamic testing is desired. The set point signal is then derived by adding together a level adjustable, direct current voltage offset signal and an amplitude adjustable alternate current voltage signal. The feedback signal, which is amplified by feedback amplification means 200, is obtained by amplifying the differential voltage which is inputted from the load transducer means, as described above. This signal can be effected by a zero adjustment knob for the purposes of creating a zero voltage output to correspond to the application of zero applied load to the test sample, i.e. prior to testing.

The set point and feedback voltage signals are then inputted to the comparator means 300. The comparator means 300 subtracts the feedback signal from the set point signal and amplifies the difference by an adjustable amount or gain.

The comparator means output signal is then inputted to the power amplification means 400 which boosts the signal power necessary for driving the actuator means and filters out high frequency noise. Preferably, the power amplification means includes a 17.5 Hz cut-off frequency. The output of the power amplification means 400 is then outputted from the controller means to drive the actuator means.

The load cycle counter means 500 receives its signal from the feedback amplification means output signal. The cycle counter has an adjustable counter set point and signals a digital cycle counter to count one number for each load cycle. This feature is primarily used for fatigue testing of samples where the number of load cycles applied is an important test parameter. Therefore, it may be disengaged or not included where "load to failure" tests are used, such as ultimate tensile and compression strength tests.

The power trip circuit means 600 receives its signal from the power amplification means output. Should the signal exceed an internally set value, the power trip circuit means immediately shuts off the power to the controller. This serves two important purposes. First, it protects the actuator from an overvoltage condition which may damage the solenoid and, second, because a test specimen failure results in the loss of the feedback signal and a large voltage output from the comparator means 300 and power amplification means 200, the power trip circuit means 600 serves as a sample failure sensor. Thus, when the test sample fails, the controller means immediately shuts the system off. Because the cycle counter means contains its own power supply, preferably batteries, the load cycle counter means 500 will retain its count when the controller means power is tripped by the power trip circuit means 600.

One specific application for the mechanical testing apparatus described by this invention is for fatigue testing of the interfacial bond formed between a single fiber and a polymeric microdroplet, i.e. sample 17. This involves the application of cyclic controlled loading between about 0.5 and 15.0 grams, preferred. To perform a test, a polymer/fiber sample 17 is attached to the load transducer means so that the opposite end of the fiber passes through the microdroplet grip or slot 41 with the microdroplet suspended slightly below the gripping surface or lower plate 40. The controller means is turned on and the feedback signal knob is adjusted until a zero voltage signal is obtained to correspond to a zero applied load. The microdroplet is then seated in the grip 21 by adjustment of the grip height. The load cycle counter means is reset to zero and its counting set point adjusted to count according to the desired load signal to be applied. With the feedback signal being preferably monitored by an externally connected oscilloscope and voltmeter, the load set point signal is adjusted until the feedback signal corresponds to the desired load program to be applied to the test sample. For example, a sine-waveform with a maximum equal to about 10.0 grams and a minimum load equal to about 1.0 grams could be used. Once the load program is set, the controller means will maintain it while counting the number of applied load cycles. This will continue until the test sample fatigues to failure, at which point the power trip circuit means 600 will shut off the control means power, thus ending the test. The number of cycles to failure will then be maintained on the load cycle counter means 500 until it is manually reset for the next run.

From the foregoing, it can be realized that this invention provides improved mechanical testing apparatus for closed-loop control, especially for controlled load fatigue testing. By using a simple, electrically operated solenoid as the test machine actuator, and coupling it with a sensitive feedback transducer, this invention develops a very simple and inexpensive closed-loop test machine specifically designed for extremely small load and displacement mechanical testing. The preferred embodiments should be attractive to anyone seeking to perform mechanical tests on very delicate materials requiring the accurate application of very small loads and displacements. Although various embodiments have been illustrated, this was for the purpose of describing, but not limiting, the invention. Various modifications, which will become apparent to one skilled in the art, are within the scope of this invention described in the attached claims.

The following specifications are applicable to the preferred embodiment circuitry of FIG. 4. These specifications are intended as a guide and are not designed to limit the invention in any manner.

| ITEM NO. | NAME | VALUE, DESCRIPTION, ETC. |
| --- | --- | --- |
| 100 | SET POINT CONTROL | |
| 102 | Amp Adj | 1KΩ 10T POT |
| 104 | DC Offset | 1KΩ 10T POT |
| 106 | RESISTOR | 15KΩ 0.1% |
| 108 | RESISTOR | 15KΩ 0.1% |
| 110 | AMPLIFIER | VOLTAGE ADDER LH0044 |
| 112 | RESISTOR | 15KΩ 0.1% |
| 114 | RESISTOR | 5KΩ 0.1% |
| 200 | FEED BACK AMPLIFIER | |
| 202 | AMPLIFIER | TRANSDUCER AMPLIFIER 400x LH0038 CD |
| 204 | RESISTOR | 130KΩ 0.1% |
| 206 | RESISTOR | 30KΩ 0.1% |
| 208 | RESISTOR | 130kΩ 0.1% |
| 210 | POT | TRANSDUCER ZEROING POT 2KΩ, 10T |
| 300 | SETPOINT-FEEDBACK COMPARATOR | |
| 302 | SWITCH | TRANSDUCER CALIBRATION SWITCH |
| 304 | POT | GAIN ADJ. POT 100K 15T |
| 306 | RESISTOR | 500Ω 1% |
| 308 | AMPLIFIER | SET POINT-FDBK DIFF. AMPLIFIER LH0036CG |
| 400 | POWER AMPLIFIER FILTER | |
| 402 | CAPACITOR | 1.0μ F |
| 404 | RESISTOR | 10KΩ 1% |
| 406 | RESISTOR | 10kΩ 1% |
| 408 | RESISTOR | 10KΩ 1% |
| 410 | RESISTOR | 10KΩ 1% |
| 412 | AMPLIFIER | L.P. FILTER POWER AMP LH0021CK fc = 17.5Hz |
| 414 | CAPACITOR | 1.0μ F |
| 500 | LOAD CYCLE COUNTER | |
| 502 | COUNTER | LOAD CYCLE COUNTER DIGITAL READOUT |
| 504 | TRANSISTOR | PNP |
| 506 | POT | 2KΩ CYCLE COUNTER REF. ADJUST. POT. |
| 508 | RESISTOR | 4.0KΩ |
| 510 | RESISTOR | 5.0KΩ |
| 512 | RESISTOR | 10KΩ |
| 514 | RESISTOR | 10KΩ |
| 516 | AMPLIFIER | VOLTAGE INVERTOR LF351N |
| 518 | AMPLIFIER | COUNTER COMPARATOR LF351N |
| 520 | RESISTOR | 1.3MΩ |
| 522 | RESISTOR | 47KΩ |
| 524 | DIODE | |
| 600 | POWER TRIP POWER ON/OFF | |

-continued

| ITEM NO. | NAME | VALUE, DESCRIPTION, ETC. |
| --- | --- | --- |
| 602 | RELAY | |
| 604 | RESET BUTTON | |
| 606 | DPST SWITCH | |
| 608 | LED | |
| 610 | RESISTOR | 650Ω |
| 612 | TRANSISTOR | NPN |
| 614 | RESISTOR | 6.8kΩ |
| 616 | RESISTOR | 820KΩ |
| 620 | RESISTOR | 200Ω, ½w |
| 620 | AMPLIFIER | VOLTAGE COMPARATOR 351 |
| 700 | TRANSDUCER | LOAD TRANSDUCER |
| 702 | RESISTOR | 10KΩ |
| 704 | RESISTOR | 60KΩ |
| 706 | RESISTOR | 60KΩ |

*Resistors are ¼W and 5% tolerance unless specified otherwise.

What is claimed is:

1. An apparatus for mechanically testing a sample under relatively light loads comprising:
   (a) solenoid actuator means for exerting an applied load force of up to about 200 grams upon said sample;
   (b) load transducer means for converting said applied load force into a voltage feedback signal, said load transducer means being attachable to said sample; and
   (c) closed-loop control means for regulating said applied load force by controlling said solenoid actuator means; said regulating being, at least in part, responsive to said voltage feedback signal.

2. The apparatus of claim 1 wherein said sample is disposed between said electrically-driven actuator means and said load transducer means.

3. The apparatus of claim 1 wherein said sample is disposed between said load transducer means and a gripping device.

4. The apparatus of claim 1 wherein said electrically-driven actuator comprises a solenoid.

5. The apparatus of claim 1 wherein said load transducer means comprises a strain gauge.

6. The device of claim 1 wherein said load transducer means comprises a plurality of strain gauges bonded to a flexible sheet of material.

7. The apparatus of claim 1 where said load transducer means comprises four strain gauges bonded to a flexible sheet of metal.

8. The apparatus of claim 7 wherein said strain gauges are electrically disposed in a Wheatstone-bridge arrangement.

9. The device of claim 8 wherein said flexible sheet of metal is configured to cause a generation of a strain field approximating pure bending upon an application of an axial force to said flexible sheet of metal.

10. The device of claim 9 wherein said load transducer means comprises electrical connection means for connecting said load transducer means to said closed-loop control means.

11. The device of claim 1 wherein said load transducer means weighs less than about one gram.

12. The device of claim 1 wherein said load transducer means weighs less than about 0.2 grams.

13. The device of claim 1 wherein said closed-loop control means comprises set point adjustment means for setting a level of direct current voltage offset signal and an amplitude alternate current voltage signal.

14. The apparatus of claim 13 wherein said closed-loop control means comprises feedback amplification means for amplifying said voltage feedback signal.

15. The device of claim 14 wherein said feedback amplification means comprises zero adjustment means for creating about a zero voltage output to correspond to an application of zero applied load prior to testing said sample.

16. The device of claim 14 wherein said closed-loop control means further comprises comparator means for receiving a plurality of voltage signals from said set point adjustment means and said feedback amplification means, said comparator means having means for subtracting a signal derived from said feedback amplification means from a signal derived from said set point adjustment means and for amplifying a difference between said signals.

17. The apparatus of claim 16 wherein said closed-loop control means further comprises power amplification means for boosting the output from said comparator means.

18. The apparatus of claim 17 wherein said power amplification means further comprises filtering means for filtering out high frequency noise distortion.

19. The appartus of claim 18 further comprising means for operating said electrically-driven actuator means with an output from said power amplification means.

20. The apparatus of claim 19 wherein said closed-loop control means further comprises load cycle counter means for receiving a signal from said feedback amplification means and for counting a number of load cycles.

21. The apparatus of claim 20 wherein said closed-loop control means comprises power trip circuit means for receiving a signal from said power amplification means and for shutting off power to said closed-loop control means when said signal from said power amplification means exceeds an internally set value.

22. The apparatus of claim 21 wherein said power trip circuit means comprises failure sensor means for shutting off power to said closed-loop control means when said sample fails.

23. A method for mechanically testing a sample under relatively light loads comprising:
   (a) providing a mechanical testing apparatus having electrically-driven actuator means for exerting an applied load force of not more than about 200 grams upon said sample, load transducer means for converting said applied load force to a voltage feedback signal, said load transducer means being attachable to said sample and weighing less than 10 grams, said apparatus further including closed-loop control means for at least regulating said applied load force in response, in part, to said voltage feedback signal;

(b) applying a load to said sample with said electrically-driven actuator means to a degree sufficient to cause said load transducer means to provide said voltage feedback signal to said closed-loop control means for regulating said applied load.

* * * * *